US006818777B2

(12) United States Patent
Fukuyama et al.

(10) Patent No.: US 6,818,777 B2
(45) Date of Patent: Nov. 16, 2004

(54) INTERMEDIATES FOR SYNTHESIS OF VINBLASTINE COMPOUND AND METHOD FOR SYNTHESIZING THE INTERMEDIATE

(75) Inventors: Tohru Fukuyama, Tokyo (JP); Hidetoshi Tokuyama, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 10/380,831

(22) PCT Filed: Sep. 20, 2001

(86) PCT No.: PCT/JP01/08202

§ 371 (c)(1),
(2), (4) Date: Mar. 19, 2003

(87) PCT Pub. No.: WO02/46185

PCT Pub. Date: Jun. 13, 2002

(65) Prior Publication Data

US 2004/0034217 A1 Feb. 19, 2004

(30) Foreign Application Priority Data

Dec. 7, 2000 (JP) ........................................ 2000-372508
Dec. 12, 2000 (JP) ........................................ 2000-377199

(51) Int. Cl.⁷ .................... C07D 209/12; C07D 217/08; C07D 215/12; A61K 31/47; A61K 31/404; A61K 31/18; C07C 311/08
(52) U.S. Cl. ...................... 548/494; 548/469; 548/494; 546/152; 546/156; 564/92; 564/99; 514/311; 514/312; 514/415; 514/419; 514/605
(58) Field of Search ................................ 548/469, 494; 546/152, 156; 514/415, 419, 311, 312, 605; 564/92, 99

(56) References Cited

PUBLICATIONS

Tokuyama et al, "A Practical Route to Quinolines from Anilines," Heterocycles (2001), vol. 54 (1), pp. 105–108.*
Tokuyama et al, "Asymmetric Total Synthesis of Vindoline," 26th Symposium on Progress in Organic Reactions and Synthesis, pp. 200–201, Japan Pharmaceutical Society, Oct. 27, 2000.*

Tokuyama et al, "Novel Synthetic Method of Substituted Quinoline," 40th Kanto Branch Symposium of Organic Synthetic Chemical Society, pp. 65–66, Nov. 25, 2000.*
H. Tokuyama, et al. "Assymetric Total Synthesis of Vindoline", 26th Symposium on Progress in Organic Reactions and Synthesis, pp. 200–201, Japan Pharmaceutical Society, Oct. 27, 2000.
M. Sato, et al. "A New and Practical Method for Synthesis of Substituted Quinoline" 44th Kanto Branch Symposium of Japan Pharmaceutical Society, p. 49, Sep. 22, 2000.
H. Tokuyama, et al. "Novel Synthetic Method of Substituted Quinoline", 40th Kanto Branch Symposium of Organic Synthetic Chem. Society, pp. 65–66, Nov. 25, 2000.

* cited by examiner

Primary Examiner—Ceila Chang
Assistant Examiner—Janet L. Coppins
(74) Attorney, Agent, or Firm—Sherman & Shalloway

(57) ABSTRACT

Intermediates A, which are important in the whole synthesis of vindoline; and a method of synthesizing intermediates respectively represented by the general formulae B and C. By the method, the target intermediates are effectively synthesized with satisfactory reproducibility. This synthesis method is especially suitable for mass production. General formula A General formula B General formula C.

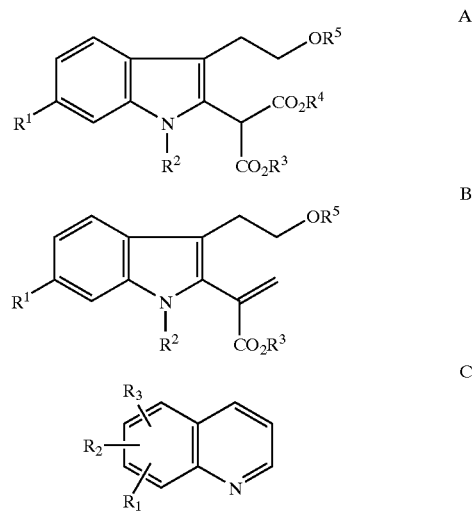

6 Claims, No Drawings

INTERMEDIATES FOR SYNTHESIS OF VINBLASTINE COMPOUND AND METHOD FOR SYNTHESIZING THE INTERMEDIATE

FIELD OF THE INVENTION

The present invention relates to a compound represented by general formula A, which is useful as intermediate at the total synthesis of vindoline, general formula A

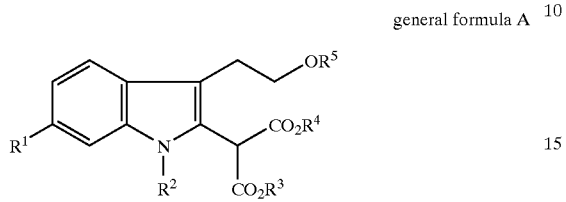

(in the formula, $R^1$ is one selected from the group consisting of H, OH, alkoxy group, substituted or non-substituted benzenesulfonyloxy group, and alkylsulfonyloxy group, $R^2$ is 1,1-dimethylethoxycarbonyl [(1,1-Dimethylethoxy) carbonyl, Boc] group or acetyl group, $R^3$ is alkyl group, $R^4$ is benzyl or substituted benzyl group. $R^5$ is H, tetrahydropyranyl (THP) group, ethoxyethyl group, methoxymethyl group, acetyl group, benzoyl group, trialkylsilyl group or alkyldiarylsilyl group.), alkyl acrylates represented by general formula B, which is important an intermediate at the total synthesis of vindoline, general formula B

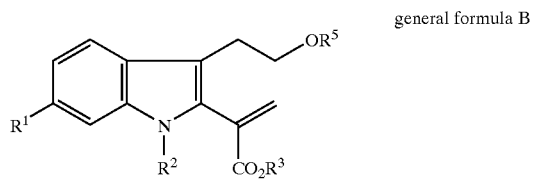

[in the formula, $R^1$ is one selected from the group consisting of H, OH, alkoxy group, substituted or non-substituted benzene sulfonyloxy group, and alkyl sulfonyloxy group, $R^2$ is 1,1-dimethylethoxycarbonyl (indicated as Boc in a constitutional formula) group or acetyl group and, $R^3$ is alkyl group. $R^5$ is H, tetrahydropiranyl (THP) group, ethoxyethyl group, methoxymethyl group, acetyl group, benzoyl group, trialkylsilyl group or alkyldiarylsilyl group.], especially relates to an effective method for synthesis of indole derivatives possessing a methyl acrylate group having good reproducibility and suited to mass production, and an effective method for production of substituted quinolines represented by general formula C, which is useful for the synthesis of said general formula A, and whose regioselectivity and yield are improved.

general formula C

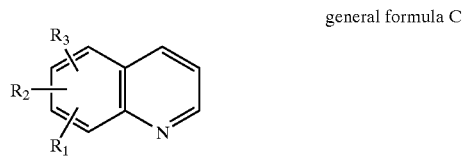

($R_1$, $R_2$ and $R_3$ are independently selected from the group consisting of H, OH, alkoxy group, alkyl, amino, amide and halogen.)

BACKGROUND OF THE INVENTION

Natural vinblastine (1) extracted from a plant belonging to Apocynaciae is an antitumor agent which is currently used as a clinical medicine. However, since this agent shows a strong side effects, the developments for a new congeners are broadly carried out in Japan or outside of Japan.

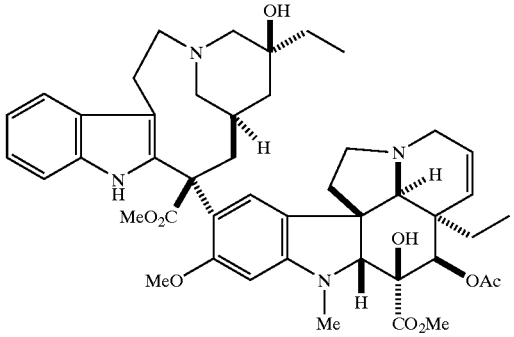

The inventors of the present invention has already reported the art referring to the total synthesis of vindoline which consists a half (lower side) of vinblastine (1) used for the synthesis of above mentioned vinblastine and its congeners. However, for the total synthesis of vindoline, syntheses of various intermediates are necessary, the improvements of the reproducibility of each processes and yield are needed, and the further improvement for process suited to the production concerning the commercial scale is needed.

Usually, the compound represented by said general formula B, which is the important intermediate for the synthesis of vindoline, was synthesized using the derivatives of above mentioned general formula A, whose substituent at 2-position is replaced with iodine, as the starting material by palladium-catalyzed coupling reaction with tin compound as shown in the following Scheme 1 [S. Kobayashi, T. Ueda, T. Fukuyama, Synlett., 883–886 (2000)].

scheme 1

However, by above mentioned reaction, it is difficult to accomplish the reaction in good yield and with good reproducibility, and further, in above mentioned reaction, there is a problem that the uses of agents such as toxic arsenic compound or carcinogeic hexamethyltriamidephosphate (HMPA) are necessary. Therefore, the establishment of the method for synthesis of above mentioned intermediate B characterizing not including above mentioned technical problems was desired. Further, as one intermediate for the synthesis of above mentioned intermediate A, quinolines represented by general formula C, namely, substituted quinoline which has a substituted group on benzene ring and does not have a substituted group on pyridine ring is used.

As the typical well-known method for synthesis for a substituted quinoline which has a substituted group on benzene ring, a method for synthesis named Skraup quinoline synthesis which obtains quinoline by heating anilines, glycerin and oxidant under the presence of strong acid such as sulfuric acid can be mentioned [R. H. F. Manske, M. Kulka, Org. React. 28, 59–98 (1953)]. However, since said method needs a process to react by high temperature using strong acid, many byproducts are generated besides the aimed compound. Therefore, very complicated separation and purification process is necessary to obtain the aimed product and the yield by said method is not always good. Further, in a synthetic reaction of substituted quinoline which uses meta substituted aniline or 2,3-disubstituted aniline as a starting material, mixture of 5-substituted quinoline and 7-substituted quinoline, or mixture of 6,7-substituted quinoline and 5,6-substituted quinoline, which are regioisomers are generated. In the case of said mixture, sometimes one isomer has predominant over another isomer at the generation by maximum four times amount according to the substitution effect, however, in general, the regioselectivity of the reaction is not so high, and this point is pointed out as a problem [M. H. Palmer, J. Chem. Soc., 3645–3652 (1962)]. Still more, the yield is also not so good.

Furthermore, the compound represented by above mentioned general formula C is the compound used as the synthetic intermediate of general formula A, which are the intermediate at the total synthesis of vindoline. And, for the establishment of effective synthetic process for the total synthesis of vindoline, the improvement of the intermediate processes composing total synthesis is very important. Especially, the establishment of the method producing substituted quinolines, which have a substituted group on benzene ring alone and do not have a substituted group on pyridine ring, with improved regioselectivity has been strongly desired.

Therefore, the first object of the present invention is to provide a method for production of the intermediate B represented by general formula B, which dissolves the problem of above mentioned conventional art has, having good yield and reproducibility, and further, said method should be applicable to the production process of commercial scale. The inventors of the present invention have conducted an eager study to investigate the method for production of the compound represented by general formula B not by way of 2-iodoindole shown in the conventional art, and to establish the method for production by way of compound represented by general formula A. Thus the first object of the present invention is accomplished.

The second object of the present invention is to provide a method for the production of substituted quinolines by which the problems in conventional method for production of substituted quinolines have are improved. The inventors of the present invention have investigated the case to obtain the aimed compound represented by general formula C from substituted aniline by way of cyclization reaction, and have found out that the regioselectivity and the yield can be remarkably improved by using following process. Namely, as the first, sulfonamide derivative of above mentioned substituted aniline is prepared, then acrolein is added and a precursor for cyclization reaction is prepared and the precursor is used. The second object of the present invention is accomplished by use of the compound represented by general formula D at the cyclization reaction.

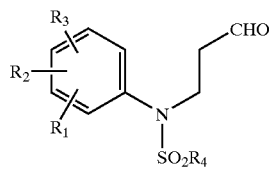

general formula D

DISCLOSURE OF THE INVENTION

The first one of the present invention is the compound represented by general formula A which is useful as the intermediate at the total synthesis of vindoline.

The second one of the present invention is a method for synthesis of indole derivatives which are useful for the synthesis of vindoline represented by general formula B comprising, hydrogenation of the compound represented by general formula A, transforming benzyl ester to carboxylic acid, then formation of an acrylic acid alkyl ester unit by Mannich reaction accompanied by decarboxylation under the condition of Mannich reaction. Desirably, the second one of the present invention is the method for synthesis of indole derivatives which are useful for the synthesis of vindoline represented by general formula B comprising, using a palladium on carbon catalyst prepared by loading palladium on activated carbon as a hydrogenation catalyst.

The third one of the present invention is a method for synthesis of the substituted quinolines represented by above mentioned general formula C by reacting substituted aniline sulfonamide compounds represented by general formula E,

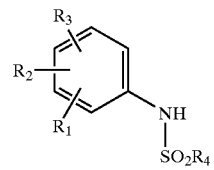

general formula E (wherein $R_1$, $R_2$ and $R_3$ is selected independently from the group consisting of H, OH, alkoxy group, alkyl group, amino group and halogen, $R_4$ is an alkyl group such as methyl group or substituted benzene, for example, p-tolyl group) in alcohol containing acrolein and triethylamine so as to synthesize aldehyde intermediate represented by general formula D, then cyclizating said aldehyde intermediate by trifluoromethanesulfonic acid [TfOH: $CF_3(SO_2)OH$] or under the acidic condition (acidification by hydrochloric acid or sulfuric acid) and obtaining dihydroquinoline derivatives represented by general formula F,

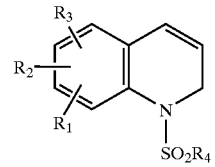

general formula F then treating the obtained dihydroquinoline derivative in MOH (M is Na or K) in DMSO, and obtaining the substituted quiloline represented by general formula C. Desirably, $R_1$ is a substitution group of 7-position and $R_2$ is a substitution group of 6-position, and each substituted group is respectively selected from the group consisting of H, hydroxyl group, alkoxy group and halogen independently and $R_3$ is H. Further, more desirably, the present invention is the method for synthesis of said substituted quinoline, wherein the cyclization reaction is carried out in tetrahydrofuran solution in which hydrochloric acid of stronger than 3N is contained.

The present invention will be illustrated more in detail.

1–1. At the first, the preparation example of the starting compound represented by general formula A is shown.

In said general formula A, the compound of $R^1$=MsO, $R^2$=Boc, $R^3$=Me, $R^4$=Bn and $R^5$=THP can be effectively synthesized by using quinoline derivative whose hydrogen of hydroxyl group located on 7-position is substituted by alkylsulfonyl group or arylsulfonyl group as a starting material. For example, phenylisothiocyanate having α,β-unsaturated aldehyde is obtained by ring-opening reaction (THF/$H_2O$ mixed solution of $Na_2CO_3$) of 7-mesyloxyquinoline with thiophosgene ($CSCl_2$) and aldehyde is reduced to alcohol and protected. Then thioamide compound is synthesized by nucleophilic addition reaction of derivatives of malonic acid (in tetrahydrofuran solution of NaH, benzylmethyl malonate is cooled by ice-bath), and the obtained thioamide compound is reacted (in the argon atmosphere) at the temperature of 80° C. in toluene solution of tri-n-butyltin hydride (n-$Bu_3SnH$) and 2,2'-azobisisobutyronitrile (AIBN). After cooled down to room temperature, saturated KF solution is added and the resulted mixture was stirred at room temperature, and then diluted with ethyl acetate. After washing with brine, organic layer is dried over magnesium sulfate anhydride and solvent is removed by vacuum. Then the residue is subjected to a silica gel column chromatography and by elution with n-hexane:ethylacetate=2:1 mixed solvent, thus indole derivative compound 1 is obtained.

compound 1

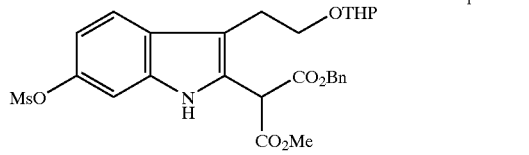

1–2. The dichloromethane solution of said compound, di-t-butyl dicarbonate, and triethylamine is cooled with ice-bath and 4-(dimethylamino)pyridine is added, then the temperature is elevated to the room temperature and stirred for 1 hour. The reaction mixture is diluted by ethyl acetate. After washing with brine, organic layer is dried over magnesium sulfate anhydride and solvent is removed by vacuum. Then the residue is subjected to a silica gel column chromatography and by elution with n-hexane:ethylacetate=2:1 mixed solvent, thus the starting material compound of general formula A, especially the starting material characterizing $R^1$=MsO, $R^2$=Boc, $R^3$=Me, $R^4$=Bn and $R^5$=THP in the compound of general formula A, can be obtained. Other compounds represented by general formula A can be synthesized by the similar method.

1–3. As the hydrogen source at the synthesis of the compound of general formula B from the compound of general formula A, ammonium formate, cyclohexene or 1,4-cyclohexadiene can be used instead of hydrogen. As a solvent, lower alcohol such as methanol or ethanol, or ethyl acetate can be used. As a catalyst for hydrogenation, palladium on carbon catalyst, palladium hydroxide or Raney nickel can be used, and as the desirable one, palladium on carbon catalyst can be mentioned.

1–4. Mannich reaction can be carried out by using a combination of formalin, dimethylamine hydrochloride, acetic acid and sodium acetate, a combination of formalin with dimethylamine hydrochloride, a combination of formalin and diethylamine with acetic acid, a combination of formalin and inorganic acid e.g. hydrochloric acid with secondary amine e.g. pyrrolizine. As the desirable combination, the combination. of formalin, dimethylamine hydrochloride, acetic acid and sodium acetate can be mentioned.

2–1. The compound of general formula E used in the present invention can be obtained by reacting substituted aniline with para-toluenesulfonyl chloride (pTsCl) or methanesulfonyl chloride (MsCl) in dichloromethane in the presence of pyridine.

Instead of using pyridine in dichloromethane, it is possible to use $M_2CO_3$ (M is Na or K) in 1,4-dioxane/water mixed solvent.

2–2. The compound of general formula D can be synthesized from the compound of general formula E by Michael addition reaction to acrolein (2–10 equivalents) in alcohol e.g. methanol in which triethylamine (0.1–2 equivalents) exists, in approximately 100% yield.

In this case, tertiary alkylamine such as diisopropylethylamine, diazabicycloundecene or diazabicyclononen can be used instead of triethylamine.

2–3. Substituted dihydroquinoline represented by general formula F can be obtained by carrying out the cyclization reaction of the compound represented by general formula D in dichloromethane solution of trifluoromethanesulfonic acid or in tetrahydrofuran (THF) or 1,4-dioxane solution of hydrochloric acid or sulfuric acid.

2–4. The compound of general formula C, which is the aimed compound of the present invention, can be obtained by treating mentioned obtained compound of general formula F by heating (at approximately 50° C. to 140° C.) in dimethylsufoxide (DMSO) in which MOH (M is Na or K) exists.

EXAMPLES

The synthetic intermediates for synthesis of vinblastine and its congeners of the present invention and the method for synthesis of said intermediates are illustrated according to the substantial Examples, however, not intending to limit the scope of the claims of the present invention.

Example 1

In the present Example, the method for synthesis of compound 2, characterizing $R_1$ of 7-position of general formula C is substituted by a hydroxyl group is illustrated.

compound 2

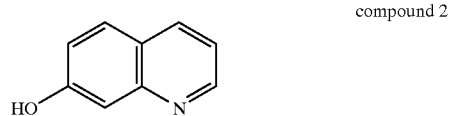

Process 1

To a pyridine solution (470 mL) of 3-aminophenol (102.6 g, 0.940 mol is added dropwise pyridine solution (500 mL) of p-toluenesulfonyl chloride (shortened to TsCl) (198 g, 0.987 mol) over 3 hours with cooling with ice-bath. After stirring for 30 minutes maintaining same temperature, the reaction mixture is diluted with ethyl acetate, then washed with brine. The water layer is extracted by ethyl acetate, the organic layer is dried over magnesium sulfate anhydride.

The solvent is removed by vacuum. In order to remove remaining pyridine the obtained residue is diluted with ether and washed with 1N hydrochloric acid. The organic layer is neutralized, washed with brine, and dried over magnesium sulfate anhydride. Solvent is condensed and removed by vacuum to give the starting material N-p-tosyl-3-hydroxyaniline (hereinafter shortened to compound 3).

Physical Property:

IR (film, cm$^{-1}$): 3260, 1600, 1493, 1304, 1149, 1091, 982, 690, 565, 543.

$^1$H NMR (400 MHz, DMSO-d$_6$): δ 2.30 (3H, s), 6.39 (1H, d, J=8.0 Hz), 6.52 (1H, d, J=7.6 Hz), 6.96 (1H, t, J=7.6 Hz), 7.32 (2H, d, J=7.6 Hz), 7.64 (2J=8.8 Hz), 9.43(1H, bs, NH), 10.1 (1H, bs, OH).

$^{13}$C NHR (100 MHz, DMSO-d$_6$): δ 21.0, 106.9, 110.6, 116.2, 126.8, 129.7, 129.9, 136.9, 139.2, 144.4, 157.9.

Analysis: Calculated data for C$_{13}$H$_{13}$NO$_3$S: C, 59.30; H, 4.98; N, 5.32.

Measured data: C, 59.14; H, 5.05; N, 5.30.

Process 2

In argon atmosphere, to the methanol solution (MeOH) (3.6 L) containing compound 3 (330 g, 0.940 mol) and triethylamine (144 ml, 1.034 mol), which is cooled with ice-bath, acrolein (330 ml, 4.7 mol) is added dropwise slowly. After the reaction completes, the reaction mixture is diluted with ethyl acetate and washed with brine. The organic component is extracted from the water layer with ethyl acetate two times, and the obtained organic layers are combined, and then methanol is evaporated by vacuum at lower temperature. The remained organic layer is dried over magnesium sulfate anhydride. The solvent is condensed and removed by vacuum to obtain 3-(N-3-hydroxyphenyl-N-p-tosylpropionaldehyde) (hereinafter shortened to compound 4). Said reaction can be indicated by the following scheme.

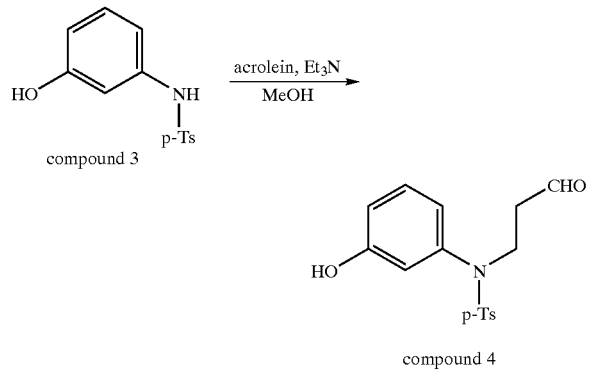

Physical Property

IR (film, cm$^{-1}$) 3430, 3029, 2736, 1720, 1595, 1483, 1455, 1343, 1218, 1161, 1089, 970, 814, 755, 693, 658, 577, 550.

$^1$H NMR (400 MHz, CDCl3): δ 2.42 (3H, s), 2.68 (2H, t, J=7.2 Hz), 3.85 (2H, t, J=7.2 Hz), 6.46 (1H, d, J=8.0 Hz), 6.70 (1H, s), 6.80 (1H, d, J=8.0 Hz), 7.13 (1H, t, J=8.0 Hz), 9.70 (1H, s, OH).

$^{13}$C NMR (100 MHz, CDCl$_3$):δ 21.5, 42.8, 44.6, 50.8, 115.7, 116.6, 119.8, 127.7, 129.6, 130.0, 134.5, 139.7, 143.9, 156.6, 200.4.

Process 3

To a tetrahydrofuran (THF) solution (1.8 L) of the compound 4 (375 g, 0.940 mol) is added hydrochloric acid of 3 N (1.8 L) slowly, and the mixture is stirred at 60° C. for 30 minutes. After reaction completes, the reaction mixture is neutralized by addition of sodium bicarbonate during cooling with ice-bath. The reaction mixture is diluted with ethyl acetate, and then washed with brine. The obtained organic layer is dried over magnesium sulfate anhydride, and the solution is condensed by vacuum to obtain 7-hydroxy-1,2-dihydroquinoline derivative (hereinafter, shortened to compound 5). Said reaction can be indicated by the following scheme.

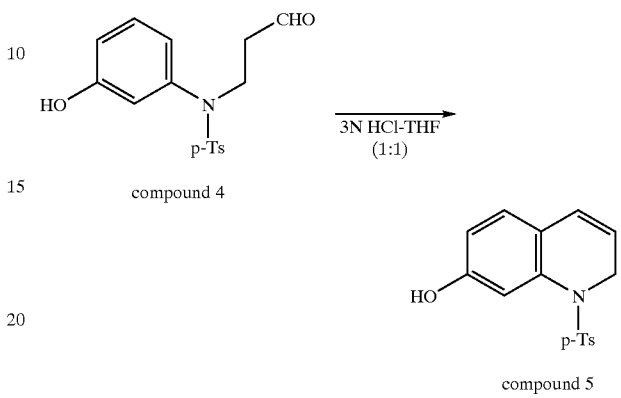

Physical Property $^1$H NMR (400 MHz, CDCl$_3$): δ 2.35 (3H, s), 4.41 (2H, dd, J=2.0, 4.0 Hz), 5.44 (1H, dt, J=4.0, 9.6 Hz), 5.98 (1H, d, J=9.6 Hz), 6.69 (1H, dd, J=2.0, 4.0 Hz), 7.08 (2H, d, J=8.8 Hz), 7.25 (1H, s), 7.35 (2H, d, J=8.0 Hz).

$^{13}$C NMR (100 MHz, CDCl$_3$):δ 21.5, 45.3, 113.7, 113.8, 120.6, 122.7, 125.1, 127.3, 127.7, 129.1, 136.1, 136.2, 143.5, 155.4.

Analysis: Calculated data for C$_{16}$H$_{15}$NO$_3$S: C, 63.77; H, 5.02; N,4.65.

Measured data: C, 61.11; H, 5.32; N, 4.31.

Process 4

In argon atmosphere, the dimethylsulfoxide solution (1.5 L) containing the compound 5 (362 g, 0.940 mol) and potassium hydroxide (248 g, 3.76 mol) is stirred at 130° C. for 30 minutes. The reaction mixture is cooled down to room temperature and cooled with ice-bath and acidified with 3 N hydrochloric acid. The obtained mixture is washed with ethyl acetate three times. Then the water layer is neutralized with sodium hydrogen carbonate, while cooling with ice-bath, and organic component is extracted from the water layer with ethyl acetate 5 to 10 times. The obtained organic extracts are dried over magnesium sulfate anhydride, and the solvent is condensed by vacuum. The obtained crude material is recrystallized from ethanol to obtain 101.5 g (72%, 4 steps) of 7-hydroxyquinoline (compound 2).

The reaction can be indicated by the following scheme.

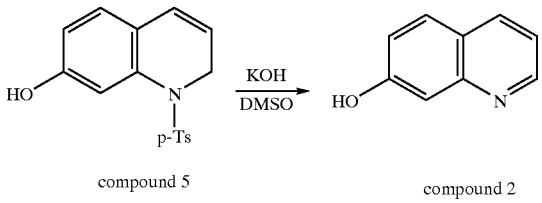

Physical Property

IR (film, cm$^{-1}$) 3423, 1610, 1503, 1336, 1293, 1162, 1089, 811, 690, 656, 582, 562, 544.

$^1$H NMR (400 MHz, DMSO-d$_6$): δ 7.17 (1H, dd, J=2.0, 8.8 Hz), 7.25 (1H, dd, J=5.2, 8.8 Hz), 7.28 (1H, d, J=2.8 Hz), 7.78 (1H, d, J=8.8 Hz), 8.16 (1H, d, J=8.0 Hz),8.73 (1H, dd, J=2.0, 5.2 Hz), 10.2 (1H, s).

$^{13}$C NMR (100 MHz, DNSO-d$_6$): δ 110.0, 118.4, 119.3, 122.3, 129.3, 135.6, 149.5, 150.5, 158.5.

Analysis: Calculated data for C$_9$H$_7$NO: C, 74.47; H, 4.86; N, 9.65.

Measured data: C, 74.28; H, 5.08; N, 9.49.

Example 2

The experimental results of the following reaction based on the present invention are shown.

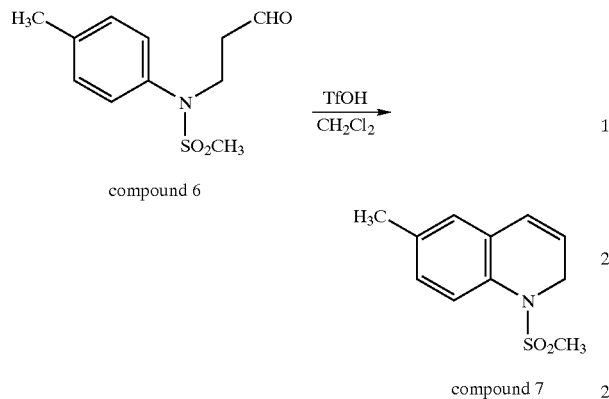

compound 6 compound 7

The compound 6 is dissolved in dichloromethane and TfOH (3.8 μL, 0.043 mmol) is added via a syringe under argon atmosphere at room temperature. The obtained mixture is stirred under argon atmosphere at 50° C. for 20 minutes. The reaction mixture is diluted with ethyl acetate and washed with saturated sodium bicarbonate. The separated water phase is extracted by ethyl acetate twice. The combined organic phase is washed with brine, dried over magnesium sulfate anhydride, filtrated, and condensed to give a crude product. The crude product is purified by a silica gel column chromatography by elution with 40% ethyl acetate/hexane to obtain dihydroquinoline derivative 7 (78 mg, 80%).

Physical Property

IR (film, cm$^{-1}$): 2930, 1490, 1346, 1336, 1158, 1065, 964, 824, 760.

$^1$H NMR (400 MHz, CDCl$_3$): δ 2.34 (s, 3H), 2.69 (s, 3H), 4.39 (m, 2H), 6.00–6.03 (m, 1H), 6.57 (d, J=10.0 Hz, 1H), 6.96 (s, 1H), 7.08 (d, J=8.0 Hz, 1H), 7.47 (d, J=8.0 Hz, 1H).

$^{13}$C NMR (100 MHz, CDCl$_3$): δ 20.9, 37.5, 45.4, 124.6, 126.4, 127.1, 127.4, 128.8, 129.1, 136.8.

HR-MS (EI) Calculated data for C$_{11}$H$_{13}$NO$_2$S: 223.0667.

Measured data: 223.0664.

Examples 3–9

Consideration about the effect of substituted group to regioselectivity and yield in the method for preparation of quinolines of the present invention.

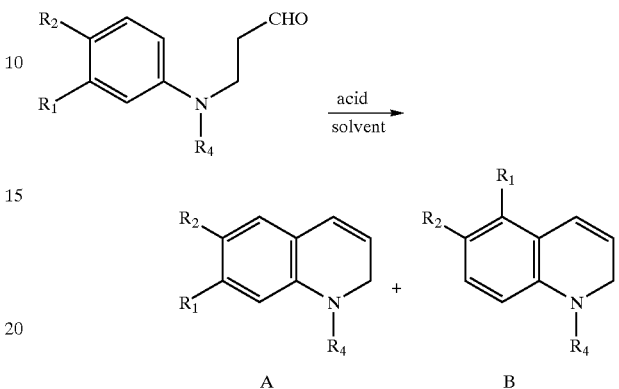

The method and results for the preparation of quinolines by way of mentioned cyclization reaction of meta- or 3,4-substituted aniline derivatives are summarized in Table 1. In Table 1, Ms=mesyl group, p-Ts=para-toluenesulfonyl group, Tf=trifluoromethanesulfonyl group, THF= tetrahydrofuran.

TABLE 1

| Example | R$_1$ | R$_2$ | R$_4$ | Acid (equivalent) | Solvent | Temp. (° C.) | Time (min.) | Yield (%) | Ratio (A:B) |
|---|---|---|---|---|---|---|---|---|---|
| 3 | H | MeO | Ms | 3N HCl | THF | 80 | 20 | 85 | 8:1 |
| 4 | H | MeO | p-Ts | 3N HCl | THF | 80 | 40 | 94 | 13:1 |
| 5 | H | OH | p-Ts | 3N HCl | THF | 80 | 20 | 82 | 14:1 |
| 6 | MeO | MeO | Ms | TfOH (0.1) | CH$_2$Cl$_2$ | 50 | 10 | 84 | 1:0 |
| 7 | H | Br | p-Ts | TfOH (1.0) | CH$_2$Cl$_2$ | rt | 10 | 88 | 3:1 |
| 8 | H | Br | p-Ts | TfOH (1.0) | CH$_2$Cl$_2$ | rt | 10 | 85 | 5:1 |
| 9 | Cl | Cl | Ms | TfOH (1.0) | CH$_2$Cl$_2$ | rt | 10 | 36 | 2:1 |

According to the ratio of regioisomers (A:B), it is clearly understood that the regioselectivity of reaction is remarkably improved compared with the conventional method for synthesis, and further, yields are remarkably improved.

Example 10

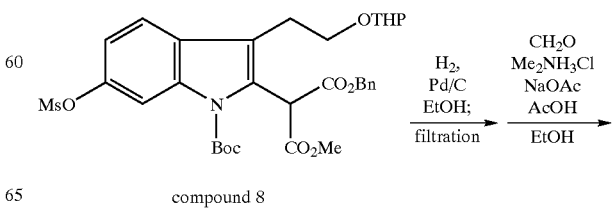

compound 8

-continued

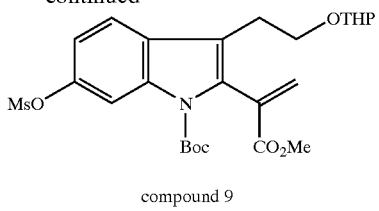

compound 9

As shown by above mentioned scheme, palladium on carbon (10 wt. % on activated carbon) (280 mg) is added to ethanol solution (35 ml) of compound 8 (2.79 g, 4.32 mmol) and stirred under hydrogen atmosphere for 6 hours. The suspension is filtrated through a pad of celite and the filter cake is then rinsed with ethanol. Without condensation of the reacted solution, formalin (5.2 ml, 65 mmol), dimethylamine hydrochloride (3.6 g, 43 mmol), sodium acetate (3.8 g, 45 mmol), and acetic acid (1.4 ml, 24 mmol) are added sequentially while cooling with ice-bath. After elevating the temperature to room temperature, the mixture was stirred at said temperature for 3 hours to overnight. After the reaction completes, the mixture is diluted by diethylether and washed with aqueous saturated sodium bicarbonate and brine. The organic layer is dried over magnesium sulfate anhydride, and solvent is condensed by vacuum. The residue is purified by silica gel column chromatography to obtain 91.93 g (85%) of aimed product from elution part using mixing solution of hexane:ethylacetate=5:1.

Physical Property:

IR (film, $cm^{-1}$): 3354, 2952, 1730, 1613, 1475, 1442, 1364, 1330, 1184, 1153, 1097, 967, 835, 758, 529.

$^1$H NMR (400 MHz, $SDCl_3$): δ 1.37–1.69 (6H, m), 1.53 (9H, s), 2.89 (2H, m), 3.09 (3H, s), 3.37 (1H, m), 3.51 (1H, q, J=6.8 Hz), 3.66 (3H, s), 3.62–3.68 (1H, m), 3.86 (1H, m), 4.50 (1H, s), 5.87 (1H, s), 6,57 (1H, d, J=2.0 Hz), 7.11(1H, dd, J=2.0, 7.6 Hz), 7.55 (1H, d, J=8.8 Hz), 8.06 (1H, d, J=1.6 Hz)

$^{13}$C NMR (100 MHz, $CDCl_3$): δ 14.2, 19.5, 25.2, 25.3, 27.8, 30.5, 37.2, 52.1, 62.2, 67.1, 85.1, 99.0, 109.8, 116.8, 118.5, 120.4, 128.6, 128.8, 133.3, 134.0, 135.6, 146.8, 149.7, 166.2.

For measurements, JASCO FT/IR-410, which is the product of Nihon Bunko Co., Ltd., is used as IR spectrometer and JEOL-LA400 of Nihon Denshi Co., Ltd., is used as a nuclear magnetic resonance spectrometer.

Reference Example
Illustration of Usefulness of Intermediate A Obtained by the Present Invention The method for synthesis of vindoline, which is a useful application of the compound obtained by the method of the present invention, will be illustrated as follows.

To the methanol solution (200 ml) of above mentioned compound 9 (7.4 g, 14 mmol) and (1S)-(+)-camphorsulfonic acid (7.3 g, 28.2 mmol) are added while cooling with ice-bath, and the resulting mixture is stirred for 2 hours. The reaction mixture is diluted by ethyl acetate, and washed with saturated sodium bicarbonate and brine. The organic layer is dried over magnesium sulfate anhydride, and solvent is condensed by vacuum. The residue is recrystallized from ethyl acetate to give the compound of general formula F. To a benzene solution (132 ml) containing compound 10 (6.67 g, 15.2 mmol), chiral amine (DNs=2,4-dinitrobenzenesulfonyl), and triphenylphosphine (6.30 g, 22.8 mmol) is added diethylazodicarboxylate (DEAD, 10.3 ml, 22.8 mol) (40% toluene solution) dropwise while cooling with ice-bath, the temperature is then elevated to room temperature. After stirring for an hour, the reaction mixture is diluted with ethyl acetate and washed with brine. The organic layer is dried over magnesium sulfate anhydride, and solvent is condensed by vacuum. The residue is purified by silica gel column chromatography by elution with n-hexane:ethyl ether=1:2 mixed solution to obtain compound 12 as yellowish powder.

To the dichloromethane solution of said compound 12 was added dimethylsulfide ($Me_2S$) at room temperature and the resulting mixture is stirred for 5 minutes maintaining same temperature, and then trifluoro acetic acid (TFA) is added dropwise. After stirring at said temperature for 5 minutes, the reaction mixture is added into the saturated sodium bicarbonate while cooling with ice-bath. The water phase is extracted twice by ethyl acetate and then twice by dichloromethane, then the extracted solutions are combined. After dried over magnesium sulfate anhydride, the solution is filtrated and condensed by vacuum. The obtained residue is dissolved in acetonitrile and methanol, to which is added pyrrolidine dropwise with cooling with ice-bath. After stirring for 5 minutes at room temperature, the temperature is elevated to 70° C. and the mixture was stirred another 3 hours. After cooling the reaction mixture to room temperature, the mixture is diluted with diethyl ether and washed twice with brine. The organic layer is dried over magnesium sulfate anhydride, the solvent is condensed by vacuum. Then the residue is purified by silica gel column chromatography by elution with n-hexane:ethyl acetate:methanol=100:50:3 mixed solution to obtain compound 13 as white powder [precursor compound of (–)-vinhydoline].

Synthetic reaction of vindoline by use of the intermediate of the present invention.

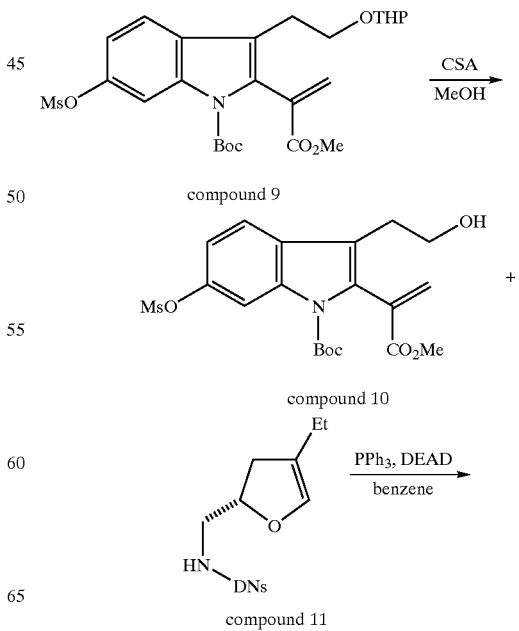

-continued

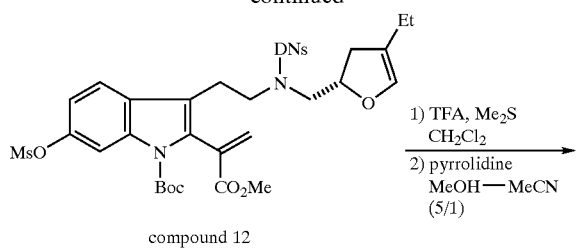

compound 12

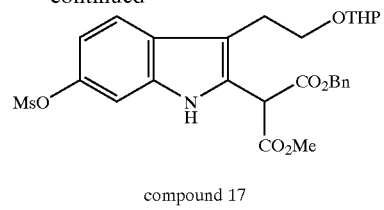

compound 17

The compound 17 is synthesized by following reactions. That is, ring-opening reaction of quiniline 13 by thiophosgene, formation of isothiocyanate, synthesis of compound 16 by nucleophilic addition reaction of malonic acid derivatives to compound 15, and reaction of compound 16, tri-n-butyltin hydride and 2,2'-azobisisobutyronitrile in toluene solution.

Industrial Applicability

As mentioned above, by the synthetic route of compound represented by general formula B, not only the yield is improved to 85%, but also the excellent effect that the toxicity of reagent used in said synthesis is smaller compared with that of above mentioned conventional art is brought. Further, the substituted quinolines represented by general formula C, which is the starting compound for the synthesis of the compound of general formula A, can be synthesized by formation of sulfonamide derivative of said substituted aniline represented by general formula E, addition of the sulfoamide to acrolein to lead the compound of general formula D, and cyclization reaction of the compound of general formula D. According to this process, the excellent function and effect that the regioselectivity and yield of the obtained compound are improved and the work-up procedure and purification process after the reaction is simplified can be brought.

Reference Example 2

For the illustration of the usefulness of the method for synthesis of quinolines of the present invention, a synthetic example of compound (compound 17) represented by general formula A from quinoline (compound 13) is shown as follows.

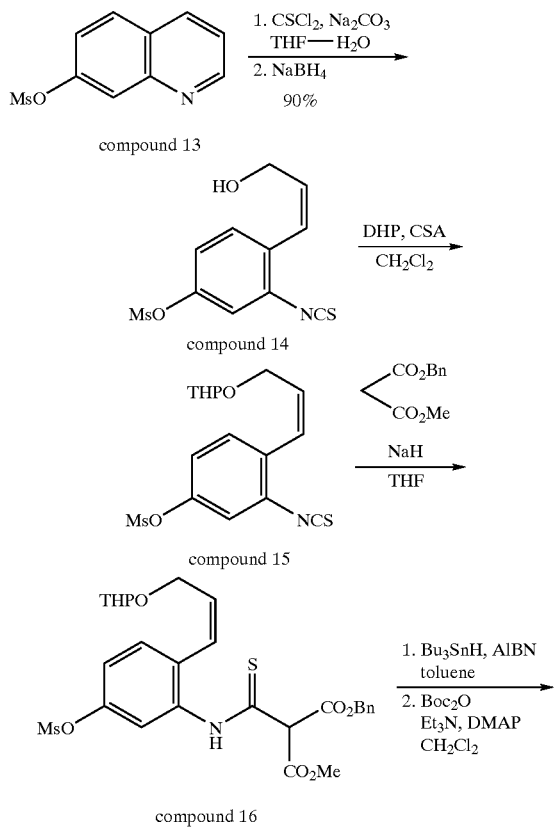

What is claimed is:

1. A compound represented by general formula A

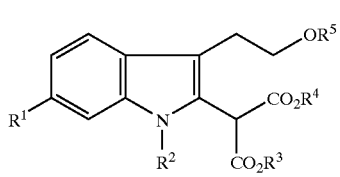

wherein, $R^1$ is one selected from the group consisting of H, OH, alkoxy group, substituted or non-substituted benzenesulfonyloxy group and alkyl sulfonyloxy group, $R^2$ is (1,1-dimethylethoxy)carbonyl group or acetyl group, $R^3$ is alkyl group, $R^4$ is benzyl or substituted benzyl group and $R^5$ is H, tetrahydropyranyl (THP) group, ethoxyethyl group, methoxymethyl group, acetyl group, benzoyl group, trialkylsilyl group or alkyldiarylsilyl group.

2. A method for synthesis of indole derivatives, which are useful for the synthesis of vindoline, represented by general formula B comprising, hydrogenation of the compound represented by general formula A, transforming benzyl ester to carboxylic acid, and then formation of an acrylic acid alkyl ester unit by Mannich reaction accompanied with decarboxylation under the condition of Mannich reaction,

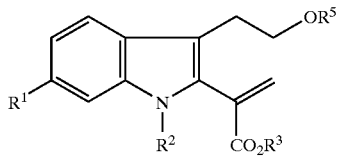

B wherein, $R^1$ is one selected from the group consisting of H, OH, alkoxy group, substituted or non-substituted benzenesulfonyloxy group, and alkylsulfonyloxy group, $R^2$ is (1,1-dimethylethoxy) carbonyl group or acetyl group, $R^3$ is alkyl group and $R^5$ is H, tetrahydropyranyl group, ethoxyethyl group, methoxymethyl group, acetyl group, benzoyl group, trialkylsilyl group or alkyldiarylsilyl group.

3. The method for synthesis of indole derivatives, which are useful for the synthesis of vindoline, represented by general formula B of claim 2 comprising, using palladium on carbon catalyst prepared by loading palladium on activated carbon as a hydrogenation catalyst.

4. A method for synthesis of the substituted quinoline represented by general formula D,

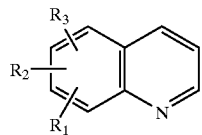

C by reacting sulfonamide derivative of substituted aniline represented by general formula E,

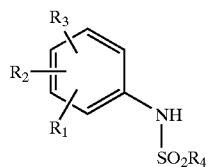

E wherein $R_1$, $R_2$ and $R_3$ is selected independently from the group consisting of H, OH, alkoxy group, alkyl group, amino group, amido group, and halogen, $R_4$ is alkyl group or substituted or non substituted benzene, in alcohol containing acrolein and triethylamine so as to synthesize aldehyde intermediate represented by general formula D,

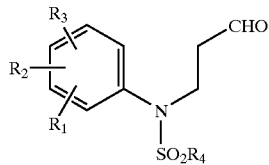

D then cyclizing said aldehyde intermediate by trifluoromethanesulfonic acid or under the acidic condition and obtaining dihydroquinoline derivatives represented by general formula F,

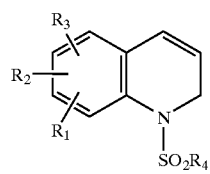

F then treating the obtained dihydroquinoline derivative in MOH, wherein M is Na or K, in DMSO.

5. The method for synthesis of substituted quinoline of claim 4, wherein $R_1$ is a substituted group of 7-position, $R_2$ is a substituted group of 6-position and each substituted group is respectively selected from the group consisting of H, hydroxyl group, alkoxy group and halogen independently and $R_3$ is H.

6. The method for synthesis of substituted quinoline of claim 5, wherein the cyclization reaction is carried out in tetrahydrofuran solution in which hydrochloric acid of stronger than 3N is contained.

* * * * *